United States Patent
Singh et al.

(10) Patent No.: US 10,287,241 B2
(45) Date of Patent: May 14, 2019

(54) METHODS AND SYSTEMS FOR PRODUCING UREA

(71) Applicant: KELLOGG BROWN & ROOT LLC, Houston, TX (US)

(72) Inventors: Vishnu D. Singh, Sugarland, TX (US); Robert K. Collins, Houston, TX (US)

(73) Assignee: KELLOGG BROWN & ROOT LLC, Houston, TX (US)

( * ) Notice: Subject to any disclaimer, the term of this patent is extended or adjusted under 35 U.S.C. 154(b) by 0 days.

(21) Appl. No.: 15/592,662

(22) Filed: May 11, 2017

(65) Prior Publication Data

US 2017/0327461 A1   Nov. 16, 2017

Related U.S. Application Data

(60) Provisional application No. 62/336,000, filed on May 13, 2016.

(51) Int. Cl.
| | | |
|---|---|---|
| *C07C 273/16* | (2006.01) | |
| *C07C 273/04* | (2006.01) | |
| *B01D 61/02* | (2006.01) | |
| *B01D 71/02* | (2006.01) | |

(52) U.S. Cl.
CPC .......... *C07C 273/04* (2013.01); *B01D 61/022* (2013.01); *B01D 61/027* (2013.01); *C07C 273/16* (2013.01); *B01D 71/024* (2013.01); *B01D 2317/022* (2013.01)

(58) Field of Classification Search
None
See application file for complete search history.

(56) References Cited

U.S. PATENT DOCUMENTS 6,538,157 B1   3/2003   Goorden et al.

*Primary Examiner* — Ana Z Muresan
(74) *Attorney, Agent, or Firm* — Gary Machetta

(57) ABSTRACT

Methods and systems for producing urea are provided. Ammonia, carbon dioxide, and a carbamate solution can be combined in a pressurized mixer to produce a carbamate reaction mixture. The carbamate reaction mixture can be transferred from the pressurized mixer to a reactor. The carbamate reaction mixture can be heated in the reactor to produce a urea reaction mixture that can include urea, water, ammonia, carbon dioxide, and ammonium carbamate. The urea reaction mixture can be contacted to a membrane to separate an aqueous filtrate and a urea concentrate that can include urea, ammonia, carbon dioxide, and ammonium carbamate. The urea concentrate can be transferred from the reactor to a urea purification system that can include one or more separators and one or more decomposers. The urea concentrate can flow through the urea purification system to produce one or more urea products and one or more carbamate solutions.

17 Claims, 2 Drawing Sheets

METHODS AND SYSTEMS FOR PRODUCING UREA

CROSS REFERENCE TO RELATED APPLICATION

This application claims priority to U.S. Provisional Patent Application having Ser. No. 62/336,000 filed May 13, 2016, which is incorporated by reference herein.

BACKGROUND

Field

Embodiments described generally relate to methods and systems for producing urea.

Description of the Related Art

Urea can be synthesized by a two reaction process that initially includes reacting ammonia and carbon dioxide to form ammonium carbamate, and subsequently, decomposing the ammonium carbamate to form urea and water. The reaction of ammonia and carbon dioxide to form urea can be described using the following equilibrium reactions:

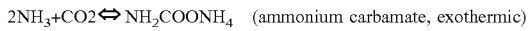
$2NH_3 + CO_2 \Leftrightarrow NH_2COONH_4$ (ammonium carbamate, exothermic)

$NH_2COONH_4 \Leftrightarrow H_2O + NH2CONH2$ (water and urea, endothermic)

The first reaction for producing ammonium carbamate is an exothermic reaction and essentially goes to completion. The second reaction for producing urea and water is endothermic and usually does not go to completion. The conversion of ammonium carbamate to urea decreases as the concentration of water or the $H_2O/CO_2$ ratio in the reaction mixture increases. In addition, the conversion of ammonium carbamate to urea increases as the temperature or the $NH_3/CO_2$ ratio increases. The resulting urea solution contains one or more contaminants, including water, ammonia, carbon dioxide, and ammonium carbamate, which must be removed to produce a purified urea product.

There is a need therefore, for improved methods and systems for making urea at increased yields and/or increased purity relative to conventional methods.

DETAILED DESCRIPTION

Methods and systems for producing urea are provided. In one or more examples, a method for producing urea can include combining ammonia, carbon dioxide, and a carbamate solution in a pressurized mixer to produce a carbamate reaction mixture that can include ammonium carbamate, ammonia, and carbon dioxide. The carbamate reaction mixture can be transferred from the pressurized mixer to a reactor. The carbamate reaction mixture can be heated in the reactor to produce a urea reaction mixture that can include urea, water, ammonia, carbon dioxide, and ammonium carbamate. The urea reaction mixture can be contacted to a membrane to separate the urea reaction mixture into an aqueous filtrate and a urea concentrate. The urea concentrate can include urea, ammonia, carbon dioxide, and ammonium carbamate. The urea concentrate can be transferred from the reactor to a urea purification system that can include one or more separators and one or more decomposers. The urea concentrate can flow through the urea purification system to produce one or more urea products and the carbamate solution. The carbamate solution can include ammonium carbamate, ammonia, and carbon dioxide.

Figure 1:
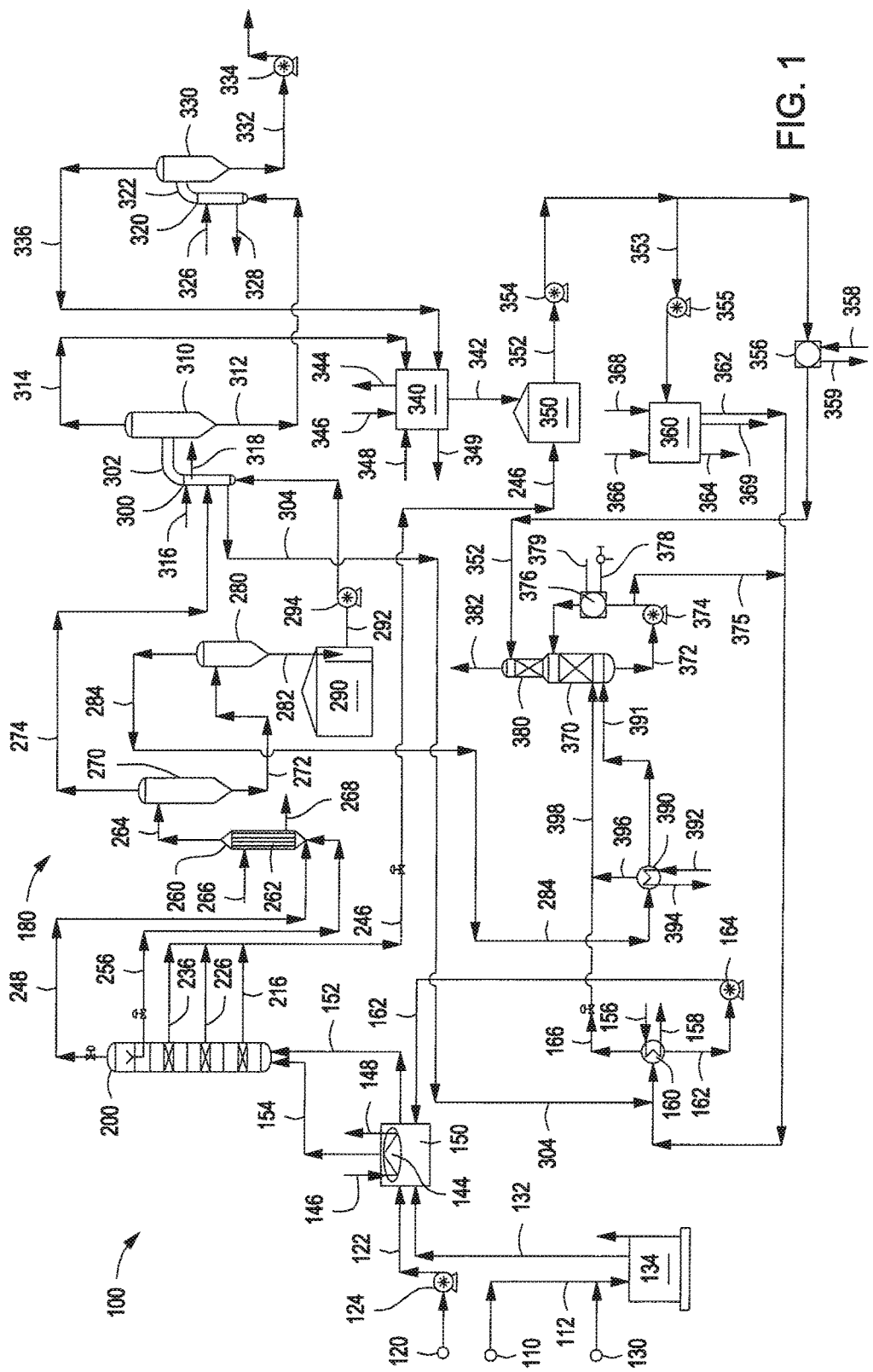
FIG. 1 depicts a schematic view of an illustrative system for producing urea, according to one or more embodiments described.

FIG. 1 depicts a schematic view of an illustrative urea production system 100 that can include one or more pressurized mixers 150 and one or more reactors 200. Ammonia and carbon dioxide can be combined and reacted in the pressurized mixer 150 to produce the carbamate reaction mixture via an exothermic reaction. The ammonium carbamate in the carbamate solution can be decomposed or otherwise reacted in the reactor 200 via an endothermic reaction to produce urea.

Ammonia via line 122 can be transferred from one or more ammonia sources 120 to the pressurized mixer 150. One or more compressors and/or one or more pumps 124 can be coupled to and in fluid communication with line 122 and can be used to assist in the transfer the ammonia to the pressurized mixer 150. The pump 124 can also be used to compress or liquefy the ammonia. The ammonia via line 122 can be in a liquid state and/or a gaseous state when introduced into the pressurized mixer 150. The ammonia can be introduced into the pressurized mixer 150 at a rate of about 550 kg/mt, about 560 kg/mt, or about 565 kg/mt to about 567 kg/mt, about 570 kg/mt, or about 575 kg/mt of urea product.

Carbon dioxide via line 132 can be transferred from one or more carbon dioxide sources 130 to the pressurized mixer 150. One or more pumps and/or one or more compressors 134 can be coupled to and in fluid communication with line 132 and can be used to compress or liquefy the carbon dioxide and can assist in the transfer the carbon dioxide to the pressurized mixer 150. For example, the carbon dioxide via line 112 can be introduced to the pump or compressor 134 from the carbon dioxide source 130. The carbon dioxide via line 132 can also be in a liquid state and/or a gaseous state when introduced into the pressurized mixer 150. The carbon dioxide can be introduced into the pressurized mixer 150 at a rate of about 720 kg/mt, about 725 kg/mt, about 730 kg/mt, or about 733 kg/mt to about 734 kg/mt, about 737 kg/mt, about 740 kg/mt, or about 745 kg/mt of urea product.

In some examples, air, oxygen, one or more oxidants, or one or more other gases, liquids, or fluids via line 132 can optionally be transferred from one or more sources 110 to the pressurized mixer 150. For example, the one or more gases, liquids, or fluids via line 112 can be transferred from the source 110 to the pump or compressor 134 with the carbon dioxide from the carbon dioxide source 130 and the carbon dioxide and one or more gases, liquids, or fluids can be transferred via line 132 to the pressurized mixer 150. The air, oxygen, one or more oxidants, or one or more other gases, liquids, or fluids via lines 112, 132 can be introduced into the pressurized mixer 150 at a rate depending, at least in part, on plant capacity.

One or more carbamate solutions via line 162 can be transferred to the pressurized mixer 150. One or more compressors and/or one or more pumps 164, such as a recycle pump, can be coupled to and in fluid communication with line 162 and can be used to assist in the transfer the carbamate solution to the pressurized mixer 150. The carbamate solution via line 162 can be or include one or more recycled products or one or more recovered products from downstream processing steps in the production of the urea. The carbamate solution via line 162 can include, but is not limited to, ammonium carbamate, ammonia, carbon dioxide, or any mixture thereof. The carbamate solution via line 162 can be introduced into the pressurized mixer depending, at least on part, on plant capacity.

In some examples, ammonia via line 122, carbon dioxide via line 132, and the carbamate solution via line 162 can be mixed or otherwise combined in the pressurized mixer 150 to produce the carbamate reaction mixture. In other examples, the carbamate solution via line 162 can be omitted or added during a later part of the urea production process; therefore, ammonia via line 122 and carbon dioxide via line 132 can be mixed or otherwise combined in the pressurized mixer 150 to produce the carbamate reaction mixture.

The pressurized mixer 150 can include one or more heat exchangers 144 to assist in the regulation or otherwise maintaining of a predetermined temperature within the pressurized mixer 150. One or more heat transfer mediums can be introduced via line 146 to the heat exchanger 144. The heat transfer medium can remove at least a portion of the heat of reaction in the pressurized mixer 150 by indirect heat exchange. The heat transfer fluid via line 148 can be recovered from the heat exchanger 144. The heat transfer medium introduced via line 146 can be, for example, boiler feed water (BFW), which can be recovered via line 148 as steam or condensate.

In some examples, a first portion of one or more compounds introduced to the pressurized mixer 150 can be used as a reagent to produce the carbamate reaction mixture. A second portion of the one or more compounds introduced to the pressurized mixer 150 can be passed through the pressurized mixer 150 and transferred via line 154 to the reactor 200 to be used to produce the urea reaction mixture. For example, a predetermined amount of carbon dioxide can be introduced to the pressurized mixer 150 so that a first portion of carbon dioxide can be used as a reagent and to cool the carbamate reaction mixture in the pressurized mixer 150 and a second portion of carbon dioxide transferred via line 154 to the reactor 200 can be used to assist in the transfer of thermal energy to the urea reaction mixture in the reactor 200.

The temperature and the pressure of the interior of the pressurized mixer 150, as well as the flow rate of incoming carbon dioxide or other fluids, can be adjusted in order to provide any desirable amounts of liquefied carbon dioxide and gaseous carbon dioxide in the pressurized mixer 150. In some examples, about 60 wt % to about 95 wt %, about 70 wt % to about 90 wt %, or about 75 wt % to about 85 wt % of the carbon dioxide introduced to the pressurized mixer 150 can be condensed to a liquefied state in the pressurized mixer 150 and about 5 wt % to about 40 wt %, about 10 wt % to about 30 wt %, or about 15 wt % to about 25 wt % of the carbon dioxide introduced to the pressurized mixer 150 can be transferred in a gaseous state via line 154 to the reactor 200.

The mixture of liquefied carbon dioxide and gaseous carbon dioxide can be separated by physical states in the pressurized mixer 150 in order to utilize carbon dioxide as a heat transfer media in both the first and second stages of the urea production. For example, at least a portion of the liquefied carbon dioxide can be consumed as a reagent to produce ammonium carbamate in the pressurized mixer 150. Also, since the ammonium carbamate produced in the pressurized mixer 150 is an exothermic reaction, the liquefied carbon dioxide can be utilized as a heat transfer media to cool the reaction. The gaseous carbon dioxide in the pressurized mixer 150 can be transported via line 154 to the reactor 200. Since the urea produced in the reactor 200 is an endothermic reaction, the gaseous carbon dioxide can be utilized as a heat transfer media to supply thermal energy to the reaction.

Figure 2:
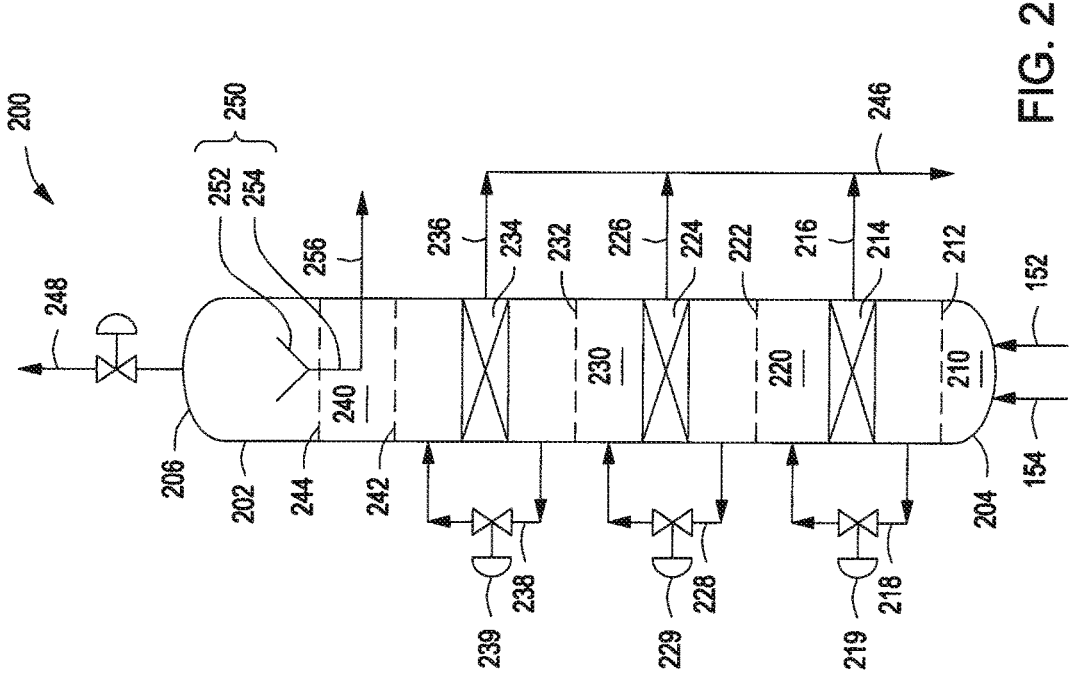
FIG. 2 depicts a partial cross sectional view of an illustrative reactor for producing urea, according to one or more embodiments described.

FIG. 2 depicts a partial cross sectional view of the reactor 200 that includes four isolated zones 210, 220, 230, 240. In other configurations not shown, the reactor 200 can include one or more isolated zones. For example the reactor 200 can include, but is not limited to, 1, 2, 3, 4, 5, 6, 8, 10, 12, or more isolated zones. The reactor 200 can include a reactor body 202 and can have a first end 204 opposite a second end 206. When the reactor 200 is in a vertically positioned, for example, the first end 204 can be the lower end or lower portion and the second end 206 can be the upper end or upper portion of the reactor 200. The isolated zones 210, 220, 230, 240 contained within the reactor body 202 can be separated or otherwise defined by a plurality of membranes 214, 224, 234. For example, the first isolated zone 210 can be disposed between the first end 204 of the reactor 200 and the first membrane 214, the second isolated zone 220 can be disposed between the first membrane 214 and the second membrane 224, the third isolated zone 230 can be disposed between the second membrane 224 and the third membrane 234, and the fourth isolated zone 240 can be disposed between the third membrane 234 and the second end 206 of the reactor 200.

In one or more examples, the reactor 200 can include at least the first isolated zone 210, the second isolated zone 220, and the third isolated zone 230. The first isolated zone 210 can include the first membrane 214, can be coupled to and downstream of the pressurized mixer 150, and can be coupled to and upstream of the second isolated zone 220. The second isolated zone 220 can include the second membrane 224, can be coupled to and downstream of the first isolated zone 210, and can be coupled to and upstream of the third isolated zone 230. The third isolated zone 230 can include the third membrane 234, can be coupled to and downstream of the second isolated zone 220, and can be upstream of the fourth isolated zone 240 and/or the urea purification system 180.

The carbamate reaction mixture via line 152 can be transferred from the pressurized mixer 150 to the first isolated zone 210 within the reactor 200. Similarly, the gaseous carbon dioxide in the pressurized mixer 150 can be transported via line 154 to the first isolated zone 210. The carbamate reaction mixture in the reactor 200, including, but not limited to, each of the isolated zones 210, 220, 230, 240, can be heated to a temperature of about 160° C., about 170° C., about 175° C., about 180° C., or about 185° C. to about 195° C., about 205° C., about 210° C., about 220° C., or about 230° C. and pressurized to a pressure of about 140 kg/cm² abs, about 160 kg/cm² abs, or about 180 kg/cm² abs to about 210 kg/cm² abs, about 225 kg/cm² abs, or about 250 kg/cm² abs for a time period of about 10 min, about 20 min, about 30 min, or about 40 min to about 60 min, about 75 min, about 90 min, or about 120 min, or more to produce the urea reaction mixture.

The carbamate reaction mixture can be heated to produce a first urea reaction mixture in the first isolated zone 210. One or more trays 212 can be disposed within the first isolated zone 210. The trays 212 can be used to control the flow rate of the carbamate reaction mixture flowing or passing within the first isolated zone 210 and therefore can be used to control the production rate of the first urea reaction mixture. Before separating any products, reagents, or other components, the first urea reaction mixture can include, but is not limited to, urea, water, ammonia, carbon dioxide, and ammonium carbamate. The first urea reaction mixture can include equal molar amounts of urea and water via the decomposition of ammonium carbamate. The first urea reaction mixture produced in the first isolated zone 210 can include about 25 wt %, about 28 wt %, about 32 wt %, or about 35 wt % to about 40 wt %, about 45 wt %, about 47 wt %, or about 50 wt % of urea, based on a combined weight of the urea, water, ammonia, carbon dioxide, and ammonium carbamate.

The first urea reaction mixture can be exposed or otherwise contacted to a first membrane 214 contained within the first isolated zone 210 to separate a first aqueous filtrate and a first urea concentrate. In some examples, the first urea reaction mixture, in combination with the carbamate reaction mixture, can be partially in contact or can be continuously in contact with the first membrane 214 while being produced in the first isolated zone 210. As the decomposition reaction of the ammonium carbamate in the carbamate reaction mixture advances, molar equivalents of urea and water can be produced in the first isolated zone 210. The majority of the water in the first urea reaction mixture can be flowed or otherwise passed through the first membrane 214 to produce the first aqueous filtrate. The remainder of the first urea reaction mixture not flowed through the first membrane 214 can pass along the first membrane 214 to produce the first urea concentrate.

The first aqueous filtrate can include mostly water, but can also include lesser amounts of ammonia, carbon dioxide, and/or urea. In some examples, the first aqueous filtrate can include about 80 wt % to about 99.9 wt % of water, about 0.5 wt % to about 15 wt % of ammonia, about 0.05 wt % to about 10 wt % of carbon dioxide, and about 0.05 wt % to about 3 wt % of urea, based on the total weight of water, ammonia, carbon dioxide, and urea. In other examples, the first aqueous filtrate can include about 85 wt % to about 99 wt % of water, about 1 wt % to about 10 wt % of ammonia, about 0.1 wt % to about 8 wt % of carbon dioxide, and about 0.1 wt % to about 2 wt % of urea, based on the total weight of water, ammonia, carbon dioxide, and urea. In other examples, the first aqueous filtrate can include about 88 wt % to about 98 wt % or about 90 wt % to about 94 wt % of water, about 2 wt % to about 10 wt % or about 3 wt % to about 7 wt % of ammonia, about 0.5 wt % to about 5 wt % or about 1 wt % to about 3 wt % of carbon dioxide, and about 0.3 wt % to about 1.7 wt % or about 0.5 wt % to about 1.5 wt % of urea, based on the total weight of water, ammonia, carbon dioxide, and urea. The first aqueous filtrate via line 216 can be transferred from the first membrane 214 to a combined aqueous filtrate in line 246.

The first urea concentrate can include urea, ammonia, carbon dioxide, and ammonium carbamate, and can include trace amounts of water. The first urea concentrate via line 218 can be transferred from the first isolated zone 210 to the second isolated zone 220 within the reactor 200. One or more valves 219 fluidly and operably coupled to line 218 can be used to control the transfer rate of the first urea concentrate from the first isolated zone 210 to the second isolated zone 220 via line 218.

Once in the second isolated zone 220, the first urea concentrate can be heated to produce additional urea and water as a second urea reaction mixture therein. It should be noted that the composition of the second urea reaction mixture can be equivalent to the composition of the first urea concentrate less ammonium carbamate and containing the additional urea and water and any other products formed by the decomposition reaction in the second isolated zone 220.

One or more trays 222 can be disposed within the second isolated zone 220. The trays 222 can be used to control the flow rate of the first urea concentrate flowing or passing within the second isolated zone 220 and therefore can be used to control the production rate of additional urea and water (e.g., the second urea reaction mixture). Before separating any products, reagents, or other components, the second urea reaction mixture can include, but is not limited to, urea, water, ammonia, carbon dioxide, and ammonium carbamate. The second urea reaction mixture forms equal molar amounts of urea and water via the decomposition of ammonium carbamate.

The second urea reaction mixture can be exposed or otherwise contacted to a second membrane 224 contained within the second isolated zone 220 to separate a second aqueous filtrate and a second urea concentrate. In some examples, the second urea reaction mixture, in combination with the first urea concentrate, can be in partially or continuously in contact with the second membrane 224 while from being produced in the second isolated zone 220. As the decomposition reaction of the ammonium carbamate in the carbamate reaction mixture advances, molar equivalents urea and water are produced in the second isolated zone 220. The majority of the water in the second urea reaction mixture can be flowed or otherwise passed through the second membrane 224 to produce the second aqueous filtrate. The remainder of the second urea reaction mixture not flowed through the second membrane 224 can pass along the second membrane 224 to produce the second urea concentrate.

The second aqueous filtrate can include mostly water, but can also include lesser amounts of ammonia, carbon dioxide, and/or urea. In some examples, the second aqueous filtrate can include about 80 wt % to about 99.9 wt % of water, about 0.5 wt % to about 15 wt % of ammonia, about 0.05 wt % to about 10 wt % of carbon dioxide, and about 0.05 wt % to about 3 wt % of urea, based on the total weight of water, ammonia, carbon dioxide, and urea. In other examples, the second aqueous filtrate can include about 85 wt % to about 99 wt % of water, about 1 wt % to about 10 wt %/o of ammonia, about 0.1 wt % to about 8 wt % of carbon dioxide, and about 0.1 wt % to about 2 wt % of urea, based on the total weight of water, ammonia, carbon dioxide, and urea. In other examples, the second aqueous filtrate can include about 88 wt % to about 98 wt % or about 90 wt % to about 94 wt % of water, about 2 wt % to about 10 wt % or about 3 wt % to about 7 wt % of ammonia, about 0.5 wt % to about 5 wt % or about 1 wt % to about 3 wt % of carbon dioxide, and about 0.3 wt % to about 1.7 wt % or about 0.5 wt % to about 1.5 wt % of urea, based on the total weight of water, ammonia, carbon dioxide, and urea. The second aqueous filtrate via line 226 can be transferred from the second membrane 224 to the combined aqueous filtrate in line 246.

The second urea concentrate can include urea, ammonia, carbon dioxide, and ammonium carbamate, and can include trace amounts of water. The second urea concentrate via line 228 can be transferred from the second isolated zone 220 to the third isolated zone 230 within the reactor 200. One or more valves 229 fluidly and operably coupled to line 228 can be used to control the transfer rate of the second urea concentrate from the second isolated zone 220 to the third isolated zone 230 via line 228.

The second urea concentrate can be heated to produce a third urea reaction mixture in the third isolated zone 230. It should be noted that the composition of the third urea reaction mixture can be equivalent to the composition of the second urea concentrate less ammonium carbamate and containing the additional urea and water and any other products formed by the decomposition reaction in the third isolated zone 230. One or more trays 232 can be disposed within the third isolated zone 230. The trays 232 can be used to control the flow rate of the second urea concentrate flowing or passing within the third isolated zone 230 and therefore can be used to control the production rate of additional urea and water (e.g., the third urea reaction mixture). Before separating any products, reagents, or other components, the third urea reaction mixture can include, but is not limited to, urea, water, ammonia, carbon dioxide, and ammonium carbamate. The third urea reaction mixture forms equal molar amounts of urea and water via the decomposition of ammonium carbamate.

The third urea reaction mixture can be exposed or otherwise contacted to a third membrane 234 contained within the third isolated zone 230 to separate a third aqueous filtrate and a third urea concentrate. In some examples, the third urea reaction mixture, in combination with the second urea concentrate, can be partially in contact or can be continuously in contact with the third membrane 234 while from being produced in the third isolated zone 230. As the decomposition reaction of the ammonium carbamate in the carbamate reaction mixture advances, molar equivalents urea and water are produced in the third isolated zone 230. The majority of the water in the third urea reaction mixture can be flowed or otherwise passed through the third membrane 234 to produce the third aqueous filtrate. The remainder of the third urea reaction mixture not flowed through the third membrane 234 can pass along the third membrane 234 to produce the third urea concentrate.

The third aqueous filtrate can include mostly water, but can include lesser amounts of ammonia, carbon dioxide, and urea. In some examples, the third aqueous filtrate can include about 80 wt % to about 99.9 wt % of water, about 0.5 wt % to about 15 wt % of ammonia, about 0.05 wt % to about 10 wt % of carbon dioxide, and about 0.05 wt % to about 3 wt % of urea, based on the total weight of water, ammonia, carbon dioxide, and urea. In other examples, the third aqueous filtrate can include about 85 wt % to about 99 wt % of water, about 1 wt % to about 10 wt % of ammonia, about 0.1 wt % to about 8 wt % of carbon dioxide, and about 0.1 wt % to about 2 wt % of urea, based on the total weight of water, ammonia, carbon dioxide, and urea. In other examples, the third aqueous filtrate can include about 88 wt % to about 98 wt % or about 90 wt % to about 94 wt % of water, about 2 wt % to about 10 wt % or about 3 wt % to about 7 wt % of ammonia, about 0.5 wt/o to about 5 wt % or about 1 wt % to about 3 wt % of carbon dioxide, and about 0.3 wt % to about 1.7 wt % or about 0.5 wt % to about 1.5 wt % of urea, based on the total weight of water, ammonia, carbon dioxide, and urea. The third aqueous filtrate via line 236 can be transferred from the third membrane 234 to the combined aqueous filtrate in line 246.

The third urea concentrate via line 238 can be transferred from the third isolated zone 230 to the fourth isolated zone 240 within the reactor 200. One or more valves 239 fluidly and operably coupled to line 238 can be used to control the transfer rate of the third urea concentrate from the third isolated zone 230 to the fourth isolated zone 240 via line 238.

The urea concentrate can be flowed or otherwise passed through at least a portion of the fourth isolated zone 240 to one or more hoppers 250. One or more trays 242, 244 (two trays are shown in FIG. 2) can be disposed within the fourth isolated zone 240. The trays 242, 244 can be used to control the flow rate of the urea concentrate flowing through the fourth isolated zone 240 and entering into the hopper 250. The urea concentrate, before entering into the hopper 250, can emit one or more gases into the fourth isolated zone 240. The emitted gases can be or include, but are not limited to, one or more of: carbon dioxide, ammonia, water, inert gases (e.g., nitrogen and/or argon), or any mixture thereof. The emitted gases can be transferred out of the reactor 200 via line 248 for further processing. For example, the emitted gases via line 248 can be flowed or otherwise passed through and processed in the urea purification system 180.

The hopper 250, as depicted in FIG. 2, can be contained in the fourth isolated zone 240; however, in other configurations not shown, the hopper 250 can be in any isolated zone or any other portion of the reactor 200. The hopper 250 can include an inlet 252 coupled to and in fluid communication with a conduit 254. The inlet 252 can have a conical, a frusto-conical, or other shape and can be used to gather or otherwise collect the urea concentrate for entering into the conduit 254. The conduit 254 can pass through at least a portion of the reactor 200 and can be coupled to and in fluid communication with line 256.

The urea concentrate can be transferred from the hopper 250 to the urea purification system 180 via line 256, as depicted in FIG. 1. Once in the urea purification system 180, the urea concentrate and components of the urea concentrate, also referred to as the urea solution or the purified urea solution, can be further separated, concentrated, decomposed, or otherwise processed to produce multiple products. For example, the urea concentrate, components of the urea concentrate, the urea solution, and/or the purified urea solution can be flowed or otherwise passed through one, two, three, or more separators (four are shown 270, 280, 310, 330), one, two, three, or more decomposers (three are shown 260, 300, 320), and/or other components contained in the urea purification system 180 or other portions of the urea production system 100. In some examples, the urea concentrate, components of the urea concentrate, the urea solution, and/or the purified urea solution can be flowed or otherwise passed through and processed in the urea purification system 180 to produce the urea product or the urea melt via line 332 and the carbamate solution via line 162.

Figure 3:
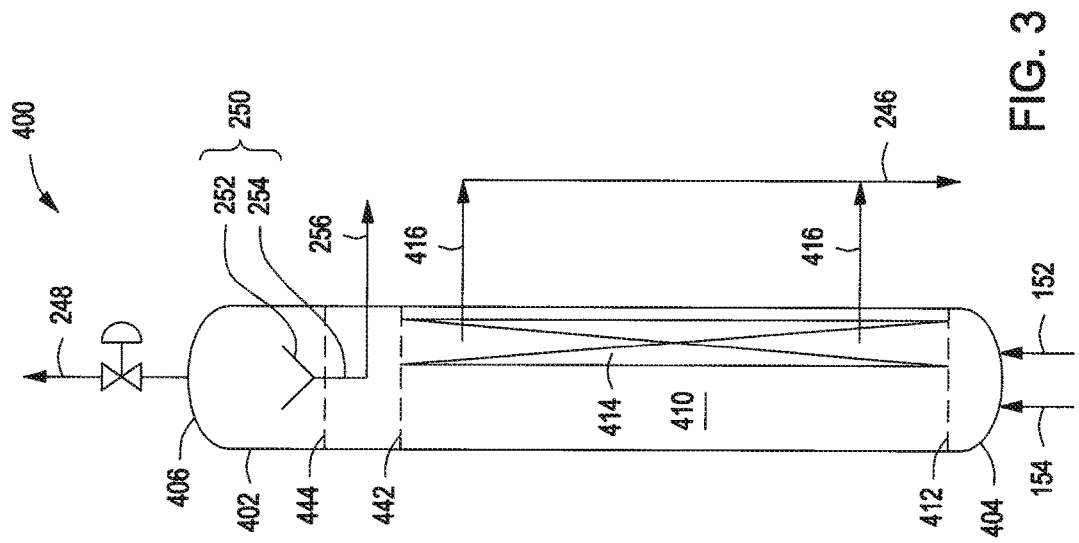
FIG. 3 depicts another partial cross sectional view of an illustrative reactor for producing urea, according to one or more embodiments described.

FIG. 3 depicts a partial cross sectional view of a reactor 400 that can be used in the production of urea. The reactor 400 can include a reactor body 402 and can have a first end 404 opposite a second end 406. When the reactor 400 is in a vertically positioned, for example, the first end 404 can be the lower end or lower portion and the second end 406 can be the upper end or upper portion of the reactor 400. The reactor 400 can include one or more reaction zones 410 and one or more membranes 414. For example, in one configuration, as depicted in FIG. 3, the reactor 400 can have a single reaction zone 410 containing a single membrane 414. In other configurations, not shown, the reactor 400 can have a single reaction zone 410 containing two or more membranes 414 or a single membrane 414 disposed within two or more reaction zones 410.

In one or more examples, the reactor 400 can substitute or replace the reactor 200 in the urea production system 100 and can be used to produce urea. In other examples, not shown, one or more other reactors can substitute or replace the reactor 200 in the urea production system 100 and can be used in the production of the urea product. The reactor 400 or portions thereof depicted in FIG. 3 and the reactor 200 or portions thereof depicted FIGS. 1 and 2 share many common components. It should be noted that like numerals shown in the Figures and discussed herein represent like components throughout the multiple embodiments disclosed herein.

The ammonium carbamate in the carbamate solution can be decomposed or otherwise reacted in the reactor 400 via an endothermic reaction to produce urea. The carbamate reaction mixture produced in the pressurized mixer 150 can be transferred via line 152 and the carbon dioxide via line 154 to the reactor 400. The carbamate reaction mixture can be heated to produce the urea reaction mixture in the reaction zone 410. One or more trays 412, 442, 444 (three trays are shown in FIG. 3) can be disposed within the reaction zone 410. The tray 412 can be used to control the flow rate of the carbamate reaction mixture and/or the urea reaction mixture flowing or passing within the reaction zone 410 and therefore can be used to control the production rate of the urea reaction mixture and the exposure rate to the membrane 414.

The urea reaction mixture, in combination with the carbamate reaction mixture, can be partially in contact or can be continuously in contact with the membrane 414 while from being produced in the reaction zone 410. The water produced in the urea reaction mixture can be flowed or otherwise passed through the membrane 414 to produce the aqueous filtrate. The remainder of the urea reaction mixture not flowed through the membrane 414 can pass along the membrane 414 to produce the urea concentrate. The aqueous filtrate via one or more lines 416 (two lines are shown in FIG. 3) can be transferred from the membrane 414 to the combined aqueous filtrate in line 246 for further processing.

The urea concentrate can be flowed or otherwise passed through at least a portion of the zone 410 to the inlet 252 of the hopper 250. The trays 442, 444 can be used to control the flow rate of the urea concentrate flowing through the reaction zone 410 and entering into the hopper 250. Once in the hopper 250, the urea concentrate can be flowed or otherwise passed through the conduit 254 and to the urea purification system 180 via line 256 for further processing and/or purification. The emitted gases via line 248 can be transferred out of the reactor 400 and can be further processed in the urea purification system 180 (FIG. 1).

The one or more membranes, e.g., membranes 214, 224, 234, 414, can independently be or include, but are not limited to, one or more of: ceramic membranes, polymeric membranes, rubber membranes, or any combinations thereof. In some examples, the membranes 214, 224, 234, 414 can independently be ceramic membranes and can include, but are not limited to, one or more of: alumina, silica, titania, zirconia, hafnia, silicon carbide, silicon oxycarbide, oxides thereof, aluminates thereof, silicates thereof, or any mixture thereof. The membranes 214, 224, 234, 414 can independently have a pore size of about 0.1 nm, about 0.2 nm, about 0.3 nm, about 0.4 nm, or about 0.5 nm to about 1 nm, about 2 nm, about 3 nm, about 4 nm, or about 5 nm. For example, the membranes 214, 224, 234, 414 can independently have a pore size of about 0.1 nm to about 5 nm or about 0.3 nm to about 2 nm. The membranes 214, 224, 234, 414 can independently a thickness of about 0.5 mm, about 0.7 mm, about 0.9 mm, or about 1 mm to about 1.5 mm, about 2 mm, about 3 mm, about 4 mm, about 5 mm, about 6 mm, about 7 mm, or about 8 mm. For example, the membranes 214, 224, 234, 414 can independently have a thickness of about 0.5 mm to about 8 mm or about 0.7 mm to about 7 mm.

The one or more trays, e.g., trays 212, 222, 232, 242, 244, 412, 442, 444, that can be disposed within the reactors 200, 400 can independently be perforated trays, sieve trays, bubble, trays, floating valve trays, fixed valve trays, cartridge trays, dual flow trays, baffle trays, shower deck trays, disc and donut trays, orbit trays, horse shoe trays, cartridge trays, snap-in valve trays, chimney trays, slit trays, or any combination thereof. The trays 212, 222, 232, 242, 244, 412, 442, 444 can independently be made from or include process inert materials. For example, the trays 212, 222, 232, 242, 244, 412, 442, 444 can independently include, but are not limited to, zirconium, titanium, nickel, chromium, stainless steel, non-ferrous metals, non-ferrous metal alloys, metal oxides, such as zirconium oxide, ceramic, glass, or any combination thereof.

Optionally, any urea concentrate, including the first, second, or third urea concentrates, can be transferred from any one or more zones, including zones 210, 220, 230, 240, 410, and/or any one or more reactors, including the reactors 200, 400, to the urea purification system 180 via line 256 and/or one or more lines not shown. In some examples, any urea concentrate can be transferred from any zone or any reactor directly to the urea purification system 180 to eventually produce the urea product, the carbamate solution, and/or other products. In one example, the second urea concentrate can be transferred from the isolated zone 230 to the urea purification system 180 to produce the urea product via line 332 and the carbamate solution via line 162.

The urea purification system 180 can include one, two, three, or more separators (four are shown 270, 280, 310, 330), one, two, three, or more decomposers (three are shown 260, 300, 320), and/or other components of the of the urea production system 100. Once in the urea purification system 180, the urea concentrate via line 256 can be separated, concentrated, decomposed, purified, or otherwise processed to produce multiple products including, but not limited to, the urea product via line 332 and the carbamate solution via line 162.

The urea concentrate via line 256 and the emitted gases via line 248 can be introduced to a plurality of tubes 262 contained in the medium pressure decomposer 260 and subsequently into the medium pressure separator 270 via line 264. The tubes 262 and the medium pressure decomposer 260 can be heated by indirect heat exchange with a heat transfer medium introduced via line 266 to a temperature of about 120° C. to about 220° C. The medium pressure decomposer 260 can be operated at a pressure of about 2 kg/cm$^2$(abs), 4 kg/cm$^2$ (abs), or 5 kg/cm$^2$ (abs) to about 7 kg/cm$^2$ (ab), 8 kg/cm$^2$ (abs), or 10 kg/cm$^2$ (abs). The heat transfer medium can be recovered via line 268. In some examples, the heat transfer medium can be low pressure steam or medium pressure steam. For example, line 266 can be a steam supply and line 268 can be a condensate return. The tubes 262 can be of a shell-and-tube type arrangement.

The urea concentrate can be further purified and/or concentrated in the medium pressure decomposer 260 and the medium pressure separator 270 to produce a purified urea solution. The urea concentrate can be sprayed or dispersed onto, or otherwise contacted to the tubes 262 disposed within the medium pressure decomposer 260. Heat from the tubes 262, via the emitted gases and/or the heat transfer medium, can dissociate, evaporate, and/or otherwise decompose at least a portion of the ammonium carbamate in the urea concentrate to provide the purified urea solution and dissociated and/or evaporated ammonium carbamate gases. The dissociation and/or evaporation of at least a portion of the ammonium carbamate can cool the purified urea solution. The purified urea solution can be recovered from the medium pressure separator 270 via line 272 and transferred to one or more low pressure flash separators 280.

The medium pressure decomposer 260 and the medium pressure separator 270 can provide the purified urea solution via line 272, which can contain less ammonium carbamate than the urea concentrate in lines 256. The purified urea solution in line 272 can contain about 47 wt %, about 50 wt %, about 53 wt %, or about 55 wt %/o to about 60 wt %, about 63 wt %, about 65 wt %, about 67 wt %, or about 70 wt % of urea. The purified urea solution in line 272 can contain about 5 wt %, about 6 wt %, about 7 wt %, or about 8 wt % to about 9 wt %, about 10 wt %, about 11 wt %, about 12 wt %, or about 13 wt % of ammonia. In at least one example, the purified urea solution in line 272 can contain less than 10 wt %, less than 8 wt %, less than 6 wt %, less than 5 wt %, less than 4 wt %, less than 3 wt %, or less than 2 wt % of ammonia. The purified urea solution in line 272 can contain about 22 wt %, about 24 wt %, or about 25 wt % to about 27 wt %, about 28 wt %, or about 30 wt % of water. The purified urea solution in line 272 can contain about 5 wt %, about 6 wt %, about 7 wt %, or about 8 wt % to about 10 wt %, about 12 wt %, about 14 wt %, or about 16 wt % of carbon dioxide. In at least one example, the purified urea solution in line 272 can contain less than 10 wt %, less than 8 wt %, less than 6 wt %, less than 4 wt %, less than 3 wt %, less than 2 wt %, or less than 1 wt/o of carbon dioxide.

The evaporated and dissociated ammonium carbamate gases, which can include ammonia, carbon dioxide, water, and inert gases (e.g., nitrogen and/or argon) from the emitted gases introduced via line 248, can be transferred from the medium pressure decomposer 260 to the medium pressure separator 270 via line 264. The combined gases, including the evaporated and dissociated ammonium carbamate gases produced in the medium pressure separator 270, can be transferred from the medium pressure separator 270 via line 274 and can be introduced to the first vacuum decomposer 300.

In the low pressure flash separator 280, the purified urea solution can be heated to a temperature of about 100° C. to about 120° C. The flash separator 280 can flash or otherwise remove ammonium carbamate gases or flashed gases from the purified urea solution to provide the purified urea solution via line 282 to one or more urea solution tanks 290. The purified urea solution in the urea solution tank 290 can be transferred via line 292 by one or more pumps 294 to the first vacuum decomposer 300.

The purified urea solution in the urea solution tank 290 can contain about 60 wt %, about 65 wt %, about 67 wt %, or about 70 wt % to about 73 wt %, about 75 wt %, about 77 wt %, or about 80 wt %/o of urea. The purified urea solution in the urea solution tank 290 can contain about 0.3 wt %, about 0.5 wt %, about 0.7 wt %, or about 1 wt % to about 1.3 wt %, about 1.5 wt %, or about 1.7 wt % of ammonia. In at least one example, the purified urea solution in the urea solution tank 290 can contain less than 1.6 wt %, less than 1.5 wt %, less than 1.4 wt %, less than 1.3 wt %, less than 1.1 wt %, or less than 1 wt % of ammonia. The purified urea solution in the urea solution tank 290 can contain about 22 wt %, about 24 wt %, or about 25 wt % to about 26 wt %, about 27 wt %, or about 29 wt % of water.

The flashed gases produced in the flash separator 280 can include, but are not limited to, ammonia, carbon dioxide, and inert gases (e.g., nitrogen and/or oxygen). The flashed gases via line 284 can be removed from the flash separator 280 and can be introduced to one or more atmospheric condensers 390. The atmospheric condenser 390 can condense at least a portion of the ammonia and carbon dioxide in the flashed gases to provide a weak carbamate solution. The weak carbamate solution via line 391 can be transferred to a weak carbamate solution cooler unit 370 and an atmospheric scrubber 380.

The purified urea solution via line 292 and the combined gases via line 274 can be introduced into one or more vacuum decomposers, such as the first vacuum decomposer 300, and subsequently, introduced into one or more vacuum separators, such as the first vacuum separator 310, via line 302. The first vacuum decomposer 300 can be heated by indirect heat exchange with a heat transfer medium introduced via line 316 to a temperature of about 115° C., about 120° C., or about 125° C. to about 130° C., about 135° C., or about 140° C. The first vacuum decomposer 300 can be operated at a pressure of about 0.1 kg/cm$^2$ abs, about 0.2 kg/cm$^2$ abs, or about 0.3 kg/cm$^2$ abs to about 0.4 kg/cm$^2$ abs, about 0.5 kg/cm$^2$ abs, or about 0.6 kg/cm$^2$ abs. The heat transfer medium can be recovered via line 318. In some examples, the heat transfer medium can be low pressure steam or medium pressure steam. For example, line 316 can be a low steam supply and line 318 can be a condensate return. The first vacuum separator 310 can be operated at a pressure of about 0.1 kg/cm$^2$ abs, about 0.2 kg/cm$^2$ abs, or about 0.3 kg/cm$^2$ abs to about 0.4 kg/cm$^2$ abs, about 0.5 kg/cm$^2$ abs, or about 0.6 kg/cm$^2$ abs.

The purified urea solution via line 292 and the combined gases via line 274 can be sprayed or dispersed onto or otherwise contacted to a plurality of tubes (not shown) disposed within the first vacuum decomposer 300. Heat from the tubes, via the combined gases and/or the heat transfer medium, can dissociate, evaporate, and/or otherwise decompose at least a portion of the ammonium carbamate in the purified urea solution to a further purified urea solution and dissociated and/or evaporated ammonium carbamate gases. The purified urea solution and the combined gases, which include the dissociated and/or evaporated ammonium carbamate gases produced in the first vacuum decomposer 300, can be transferred to the first vacuum separator 310 via line 302. In one example, at least a portion of any remaining components derived from the dissociated and/or evaporated ammonium carbamate gases produced in the first vacuum decomposer 300 can be transferred to line 362 and a medium pressure carbamate condenser 160 via line 304. The components transferred from the first vacuum decomposer 300 via line 304 can be combined with the weak carbamate solution within line 362 before entering the medium pressure carbamate condenser 160.

The combined gases in the first vacuum separator 310, and any other gases accumulated therein, can be transferred to one or more condenser units 340 via line 314. The first vacuum decomposer 300 and the first vacuum separator 310 can provide the purified urea solution via line 312, which can contain less ammonium carbamate than the purified urea solution in line 292. The purified urea solution in line 312 can contain about 83 wt %, about 85 wt %, or about 87 wt % to about 90 wt %, about 95 wt %, or about 97 wt % of urea. The purified urea solution in line 312 can contain about 0.01 wt %, about 0.02 wt %, or about 0.05 wt % to about 0.07 wt %, about 0.1 wt %, or about 0.12 wt % of ammonia. In at least one example, the purified urea solution in line 312 can contain less than 0.1 wt %, less than 0.08 wt %, less than 0.06 wt %, or less than 0.04 wt % of ammonia. The purified urea solution in line 312 can contain about 3.7 wt %, about 4 wt %, about 4.2 wt %, about 4.4 wt %, or about 4.6 wt % to about 4.8 wt %, about 5.2 wt %, about 5.5 wt %, about 5.7 wt %, or about 5.9 wt % of water. In at least one example, the purified urea solution in line 312 can contain less than 5.5 wt %, less than 5 wt %, or less than 4.5 wt % of water. In at least one example, the purified urea solution in line 312 can contain about 0.01 wt % to about 0.02 wt % of carbon dioxide.

The purified urea solution can be recovered from the first vacuum separator 310 via line 312 and transferred to one or more vacuum decomposers, such as a second vacuum decomposer 320, and introduced into one or more vacuum separators, such as the second vacuum separator 330, via line 322. The second vacuum decomposer 320 can be heated by indirect heat exchange with a heat transfer medium introduced via line 326 to a temperature of about 130° C., about 135° C., or about 140° C. to about 145° C., about 147° C., or about 155° C. The second vacuum decomposer 320 can be operated at a pressure of about 0.015 kg/cm² abs, about 0.02 kg/cm² abs, or about 0.025 kg/cm² abs to about 0.04 kg/cm² abs, about 0.05 kg/cm² abs, or about 0.07 kg/cm² abs. The heat transfer medium can be recovered via line 328. In some examples, the heat transfer medium can be low pressure steam or medium pressure steam. For example, line 326 can be a low steam supply and line 328 can be a condensate return. The second vacuum separator 330 can be operated at a pressure of about 0.015 kg/cm² abs, about 0.02 kg/cm² abs, or about 0.025 kg/cm² abs to about 0.04 kg/cm² abs, about 0.05 kg/cm² abs, or about 0.07 kg/cm² abs.

The purified urea solution via line 312 can be sprayed or dispersed onto or otherwise contacted to a plurality of tubes (not shown) disposed within the second vacuum decomposer 320. Heat from the tubes, via the heat transfer medium, can dissociate, evaporate, and/or otherwise decompose at least a portion of the ammonium carbamate in the purified urea solution to a further purified urea solution and dissociated and/or evaporated ammonium carbamate gases. The purified urea solution and the dissociated and/or evaporated ammonium carbamate gases produced in the second vacuum decomposer 320, can be transferred to the second vacuum separator 330 via line 322.

The dissociated and/or evaporated ammonium carbamate gases in the second vacuum separator 330 can be transferred to one or more condenser units 340 via line 336. The second vacuum decomposer 320 and the second vacuum separator 330 can provide one or more urea products ("urea melt") via line 332. One or more pumps 334 can be utilized to transfer the urea product via line 332. The urea melt in line 332 can include about 85 wt %, about 90 wt %, or about 95 wt % to about 96 wt %, about 97 wt %, about 98 wt %, about 99 wt %, about 99.5 wt %, about 99.9 wt %, about 99.99 wt/o, or more of urea. For example, the urea melt in line 332 can include about 85 wt % to 99.99 wt %, about 90 wt % to 99.99 wt %, about 95 wt % to about 99.99 wt %, or about 97 wt % to about 99.99 wt % of urea. The urea melt in line 332 can include about 1 ppm, about 10 ppm, about 100 ppm, or about 0.01 wt %/o of water to less than 0.1 wt %, less than 0.5 wt %, less than 1 wt %, less than 2 wt %, or less than 3 wt % of water. For example, urea melt in line 332 can include about 0.01 wt % to less than 3 wt % of water. The concentration of the urea in the urea melt recovered via line 332 can depend on the number of vacuum separation steps employed and the desired urea melt purity. The urea melt can be further processed to provide urea-formaldehyde resins, melamine, acylureas, urethanes, melamine-formaldehyde, urea prills and granules, derivatives thereof, and combinations thereof. The urea melt in line 332 can be used as a fertilizer or in the synthesis of other fertilizers.

The condenser unit 340 can be or include one or more ejectors, one or more coolers, or one or more condensers, such as a vacuum condenser. The condenser unit 340, and any fluids passing therethrough, can be cooled by indirect heat exchange with a heat transfer medium introduced via line 348. The heat transfer medium can be recovered via line 349. In some examples, the heat transfer medium can be or include water, one or more alcohols, one or more glycols, or any mixture thereof. For example, line 348 can be a cold water or fluid supply and line 349 can be a water or fluid return.

In some examples, the combined gases from the first vacuum separator 310 via line 314 and the combined gases from the second vacuum separator 330 via line 336 can be transferred into the condenser unit 340 and cooled to produce an aqueous ammonia solution and a remaining combined gases. Steam, such as low pressure steam, can be flowed into the condenser unit 340 via line 346. The aqueous ammonia solution, the combined gases, the steam via line 346, or any mixture thereof can be transferred to the atmospheric scrubber 380 via line 344 (not shown connected to the atmospheric scrubber 380) and/or can be transferred to one or more aqueous ammonia tanks 350 via line 342. For example, the combined gases can be transferred to the atmospheric scrubber 380 via line 344 and the aqueous ammonia solution can be transferred to one or more aqueous ammonia tanks 350 via line 342.

Any aqueous solutions or filtrates can be transferred to the aqueous ammonia tank 350. The aqueous filtrates via lines 216, 226, 236 can be flowed separately or together, in any combination, to the aqueous ammonia tank 350 via line 246. For example, the aqueous filtrates via lines 216, 226, 236 can be transferred from the membranes 214, 224, 234 and can be mixed, combined, or otherwise collected in line 246 to produce the combined aqueous filtrate that can be transferred to the aqueous ammonia tank 350 via line 246. The aqueous ammonia solution via line 342 can be transferred to the aqueous ammonia tank 350. The combined aqueous ammonia solution via line 352 can be transferred by one or more pumps 354 to one or more condensers or one or more coolers 356, such as an ammonia water cooler. The cooler 356 can be used to cool the combined aqueous ammonia solution by indirect heat exchange with a heat transfer medium introduced via line 358. The heat transfer medium can be recovered via line 359. In some examples, the heat transfer medium can be or include water, one or more alcohols, one or more glycols, or any mixture thereof. For example, line 358 can be a cold water or fluid supply and line 359 can be a water or fluid return. In some examples, once cooled or condensed, the combined aqueous ammonia solution can be transferred to the atmospheric scrubber 380 via line 358 for further processing. In other examples, the combined aqueous ammonia solution via lines 352, 353 can be transferred by one or more pumps 355 to one or more desorption hydrolysis units 360.

The desorption hydrolysis unit 360 can include one or more ejectors, one or more coolers, or one or more condensers and can be used to further process the combined aqueous ammonia solution from the aqueous ammonia tank 350. The desorption hydrolysis unit 360, and any fluids passing therethrough, can be cooled by indirect heat exchange with a heat transfer medium introduced via line 368. The heat transfer medium can be recovered via line 369. In some examples, the heat transfer medium can be or include water, one or more alcohols, one or more glycols, or any mixture thereof. For example, line 368 can be a cold water or fluid supply and line 369 can be a water or fluid return.

In some examples, the combined aqueous ammonia solution via lines 352, 353 can be transferred into the desorption hydrolysis unit 360 and can be treated by one or more acid sources and/or one or more steam sources to produce a condensate and a weak carbamate solution. Steam, such as high pressure and/or low pressure steam, can be flowed into the desorption hydrolysis unit 360 via line 366. The condensate can be transferred to an offsite polisher via line 364 and the weak carbamate solution can be transferred to the medium pressure carbamate condenser 160 via line 362.

One or more coolers or one or more condensers 160, such as a medium pressure carbamate condenser 160, and any fluids passing therethrough, can be cooled by indirect heat exchange with a heat transfer medium introduced via line 156. The heat transfer medium can be recovered via line 158. In some examples, the heat transfer medium can be or include water, one or more alcohols, one or more glycols, or any mixture thereof. For example, line 156 can be a cold water or fluid supply and line 158 can be a water or fluid return.

The weak carbamate solution can be transferred through and condensed by the medium pressure carbamate condenser 160 and subsequently flowed to the weak carbamate solution cooler unit 370 via lines 166, 398. Alternatively, the weak carbamate solution can be transferred through and condensed by the medium pressure carbamate condenser 160 to produce a condensed carbamate solution that can contain ammonium carbamate, ammonia, and carbon dioxide. The condensed carbamate solution can be recycled or otherwise introduced to the pressurized mixer 150 via line 162. One or more pumps 164 can be used to transfer the condensed carbamate solution to the pressurized mixer 150 via line 162.

One or more gases, liquids, and/or fluids via at least one or more lines 346, 352, 372, 391, 398 can be flowed separately or together, in any combination, to one or more weak carbamate solution cooler units 370 coupled to and in fluid communication with one or more atmospheric scrubbers 380. Once the fluids have passed through the atmospheric scrubbers 380, the scrubbed fluids can be vented to the ambient atmosphere via line 382. In some examples, a combination of two or more gases, liquids, and/or fluids via at least one or more lines 346, 352, 372, 391, 398 can be combined and passed through the weak carbamate solution cooler unit 370 and/or the atmospheric scrubber 380.

The cooled fluids can be recirculated through the weak carbamate solution cooler unit 370 via line 372. The cooled fluids can be transferred by one or more compressors or one or more pumps 374 via line 372. In some examples, the cooled fluids can be transferred via line 375 to the weak carbamate solution which the combination thereof can be transferred to the medium pressure carbamate condenser 160 via line 362.

In other examples, the cooled fluids, any other fluid passing therethrough, can be passed through one or more condensers or one or more coolers 376, such as a weak carbamate solution cooler 370 via line 372. The fluids can be cooled by indirect heat exchange with a heat transfer medium introduced via line 378. The heat transfer medium can be recovered via line 379. In some examples, the heat transfer medium can be or include water, one or more alcohols, one or more glycols, or any mixture thereof. For example, line 378 can be a cold water or fluid supply and line 379 can be a water or fluid return.

In some examples, the flashed gases can be introduced to the uncondensed gases in line 284, 396 which can then be introduced to the atmospheric condenser 390. In other examples, the gases or fluids via line 166 can be combined with the gases fluids via line 396 to produce a fluid mixture via 398 which can then be introduced to the atmospheric condenser 390. The atmospheric condenser 390 can condense at least a portion of the ammonia and carbon dioxide in the gases to provide a weak carbamate solution via line 391 and uncondensed gases via line 398. The weak carbamate solution via line 391 can be transferred to the weak carbamate solution cooler unit 370 and subsequently to the atmospheric scrubber 380.

The atmospheric condenser 390, or another type of condenser, and any fluids passing therethrough, can be cooled by indirect heat exchange with a heat transfer medium introduced via line 392. The heat transfer medium can be recovered via line 394. In some examples, the heat transfer medium can be or include water, one or more alcohols, one or more glycols, or any mixture thereof. For example, line 392 can be a cold water or fluid supply and line 394 can be a water or fluid return.

In one or more examples, the urea production system 100 can include the pressurized mixer 150 that can be coupled to and in fluid communication independently with each of the ammonia source 120, the carbon dioxide source 130, and the ammonium carbamate source, such as from the medium pressure carbamate condenser 160 via line 162. The reactor 200 can be coupled to and in fluid communication with the pressurized mixer 150 and can include the first isolated zone 210, the second isolated zone 220, and the third isolated zone 230. The urea purification system 180 can be in fluid communication with and disposed downstream of the reactor 200. In some examples, the first isolated zone 210 can include the first membrane 214, can be coupled to and downstream of the pressurized mixer 150, and can be coupled to and upstream of the second isolated zone 220. The second isolated zone 220 can include the second membrane 224, can be coupled to and downstream of the first isolated zone 210, and can be coupled to and upstream of the third isolated zone 230. The third isolated zone 230 can include the third membrane 234, can be coupled to and downstream of the second isolated zone 220, and can be upstream of the urea purification system 180. The urea purification system 180 can include two or more separators 270, 280, 310, 330 and two or more decomposers 260, 300, 320.

Embodiments described herein further relate to any one or more of the following paragraphs:

1. A method for producing urea, comprising: combining ammonia, carbon dioxide, and a carbamate solution in a pressurized mixer to produce a carbamate reaction mixture comprising ammonium carbamate, ammonia, and carbon dioxide; transferring the carbamate reaction mixture from the pressurized mixer to a reactor, heating the carbamate reaction mixture in the reactor to produce a urea reaction mixture comprising urea, water, ammonia, carbon dioxide, and ammonium carbamate; contacting the urea reaction mixture to a membrane to separate the urea reaction mixture into an aqueous filtrate and a urea concentrate comprising urea, ammonia, carbon dioxide, and ammonium carbamate; transferring the urea concentrate from the reactor to a urea purification system, wherein the urea purification system comprises one or more separators and one or more decomposers; and flowing the urea concentrate through the urea purification system to produce a urea product and the carbamate solution, wherein the carbamate solution comprises ammonium carbamate, ammonia, and carbon dioxide.

2. The method according to paragraph 1, wherein prior to transferring the urea concentrate from the reactor to the urea purification system, the method further comprises: transferring the urea concentrate through a plurality of isolated zones disposed in the reactor, wherein each isolated zone comprises an additional membrane; heating the urea concentrate in each of the isolated zones to produce additional urea and water, and contacting the urea concentrate comprising the additional urea and water to the additional membrane disposed in each of the isolated zones to separate the urea concentrate comprising the additional urea and water into the aqueous filtrate and the urea concentrate.

3. The method according to paragraph 2, further comprising collecting the aqueous filtrate from each of the membranes and combining the aqueous filtrates to produce a combined aqueous filtrate.

4. The method according to paragraph 1, wherein prior to transferring the urea concentrate from the reactor to the urea purification system, the method further comprises: transferring the urea concentrate through a plurality of isolated zones disposed in the reactor, wherein each of the plurality of isolated zones comprises a portion of the membrane; heating the urea concentrate in each of the isolated zones to produce additional urea and water, and contacting the urea concentrate comprising the additional urea and water to the portion of the membrane disposed in each of the isolated zones to separate the urea concentrate comprising the additional urea and water into the aqueous filtrate and the urea concentrate.

5. The method according to any one of paragraphs 1 to 4, wherein the membrane comprises a ceramic membrane.

6. The method according to paragraph 5, wherein the ceramic membrane has a pore size of about 0.1 nm to about 5 nm and a thickness of about 0.5 mm to about 8 mm.

7. The method according to any one of paragraphs 1 to 6, wherein the urea product comprises about 97 wt % to about 99.9 wt % of urea.

8. The method according to any one of paragraphs 1 to 7, wherein the urea purification system comprises two or more separators and two or more decomposers.

9. The method according to any one of paragraphs 1 to 8, wherein about 60 wt % to about 95 wt % of the carbon dioxide introduced to the pressurized mixer is condensed to a liquefied state in the pressurized mixer and about 5 wt % to about 40 wt % of the carbon dioxide introduced to the pressurized mixer is transferred in a gaseous state to the reactor.

10. The method according to paragraph 9, wherein the carbamate reaction mixture is transferred from the pressurized mixer to the reactor through a first line, and wherein the carbon dioxide in the gaseous state is transferred from the pressurized mixer to the reactor through a second line that is different than the first line.

11. A method for producing urea, comprising: combining ammonia and carbon dioxide in a pressurized mixer to produce a carbamate reaction mixture comprising ammonium carbamate, ammonia, and carbon dioxide; transferring the carbamate reaction mixture from the pressurized mixer to a reactor, wherein the reactor comprises a first isolated zone, a second isolated zone, and a third isolated zone, and wherein the carbamate reaction mixture is transferred from the pressurized mixer to the first isolated zone; heating the carbamate reaction mixture in the first isolated zone to produce a first urea reaction mixture comprising urea, water, ammonia, carbon dioxide, and ammonium carbamate; contacting the urea reaction mixture to a first membrane disposed in the first isolated zone to separate the urea reaction mixture into a first aqueous filtrate and a first urea concentrate comprising urea, ammonia, carbon dioxide, and ammonium carbamate; transferring the first urea concentrate to the second isolated zone; heating the first urea concentrate in the second isolated zone to produce a second urea reaction mixture comprising urea, water, ammonia, carbon dioxide, and ammonium carbamate; contacting the second urea reaction mixture with a second membrane disposed in the second isolated zone to separate the second urea reaction mixture into a second aqueous filtrate and a second urea concentrate comprising urea, ammonia, carbon dioxide, and ammonium carbamate; transferring the second urea concentrate to the third isolated zone; heating the second urea concentrate in the third isolated zone to produce a third urea reaction mixture comprising urea, water, ammonia, carbon dioxide, and ammonium carbamate; contacting the third urea reaction mixture with a third membrane disposed in the third isolated zone to separate the third urea reaction mixture into a third aqueous filtrate and a third urea concentrate comprising urea, ammonia, carbon dioxide, and ammonium carbamate; transferring the third urea concentrate from the reactor to a urea purification system; and flowing the third urea concentrate through the urea purification system to produce a urea product, wherein the urea product comprises about 95 wt % to about 99.99 wt % of urea.

12. The method according to paragraph 11, wherein the urea product comprises about 97 wt % to about 99.9 wt % of urea.

13. The method according to paragraph 11 or 12, further comprising combining a carbamate solution with the ammonia and the carbon dioxide in the pressurized mixer to produce the carbamate reaction mixture, wherein the carbamate solution comprises ammonium carbamate, ammonia, and carbon dioxide.

14. The method according to paragraph 13, wherein flowing the third urea concentrate through the urea purification system further produces the carbamate solution.

15. The method according to any one of paragraphs 11 to 14, wherein the carbamate reaction mixture in the first isolated zone is heated to a temperature of about 175° C. to about 210° C. and pressurized to a pressure of about 150 kg/cm$^2$ abs to about 210 kg/cm$^2$ abs to produce the first urea reaction mixture.

16. The method according to any one of paragraphs 11 to 15, wherein the first membrane, the second membrane, or the third membrane is a ceramic membrane having a pore size of about 0.1 nm to about 5 nm and a thickness of about 0.5 mm to about 8 mm.

17. The method according to any one of paragraphs 11 to 15, wherein at least one of the first membrane, the second membrane, and the third membrane is a ceramic membrane having a pore size of about 0.1 nm to about 5 nm and a thickness of about 0.5 mm to about 8 mm.

18. The method according to any one of paragraphs 11 to 17, further comprising combining the first aqueous filtrate, the second aqueous filtrate, and the third aqueous filtrate to produce a combined aqueous filtrate.

19. The method according to paragraph 18, wherein the combined aqueous filtrate comprises about 85 wt % to about 99 wt % of water, about 1 wt % to about 10 wt % of ammonia, about 0.1 wt % to about 8 wt % of carbon dioxide, and about 0.1 wt/o to about 1.5 wt % of urea.

20. A urea production system, comprising: a pressurized mixer coupled to and in fluid communication independently with each of an ammonia source, a carbon dioxide source, and an ammonium carbamate source; a reactor coupled to and in fluid communication with the pressurized mixer and comprising a first isolated zone, a second isolated zone, and a third isolated zone; and a urea purification system in fluid communication with and disposed downstream of the reactor, wherein: the first isolated zone comprises a first membrane, is coupled to and downstream of the pressurized mixer, and is coupled to and upstream of the second isolated zone, the second isolated zone comprises a second membrane and is coupled to and upstream of the third isolated zone, the third isolated zone comprises a third membrane and is upstream of the urea purification system, and the urea purification system comprises two or more separators and two or more decomposers.

21. The urea production system according to paragraph 20, wherein the first membrane, the second membrane, or the third membrane comprises a ceramic membrane.

22. The urea production system according to paragraph 20, wherein at least one of the first membrane, the second membrane, and the third membrane comprises a ceramic membrane.

23. The urea production system according to paragraph 20, wherein the first membrane, the second membrane, or the third membrane comprises a ceramic membrane having a pore size of about 0.1 nm to about 5 nm and a thickness of about 0.5 mm to about 8 mm.

24. The urea production system according to paragraph 20, wherein at least one of the first membrane, the second membrane, and the third membrane comprises a ceramic membrane having a pore size of about 0.1 nm to about 5 nm and a thickness of about 0.5 mm to about 8 mm.

25. The urea production system according to any one of paragraphs 21 to 24, wherein the ceramic membrane is configured to separate a urea reaction mixture comprising urea, water, ammonia, carbon dioxide, and ammonium carbamate into an aqueous filtrate and a urea concentrate comprising urea, ammonia, carbon dioxide, and ammonium carbamate.

26. A urea production system, comprising: a pressurized mixer coupled to and in fluid communication independently with each of an ammonia source, a carbon dioxide source, and an ammonium carbamate source; a reactor coupled to and in fluid communication with the pressurized mixer and comprising a first isolated zone and a second isolated zone; and a urea purification system in fluid communication with and disposed downstream of the reactor, wherein the first isolated zone comprises a first membrane, is coupled to and downstream of the pressurized mixer, and is coupled to and upstream of the second isolated zone, and wherein the second isolated zone comprises a second membrane and is coupled to and upstream of the urea purification system.

27. The urea production system according to paragraph 26, wherein the urea purification system comprises two or more separators and two or more decomposers.

28. The urea production system according to paragraph 26 or 27, wherein the first membrane comprises a ceramic membrane.

29. The urea production system according to paragraph 28, wherein the ceramic membrane has a pore size of about 0.1 nm to about 5 nm and a thickness of about 0.5 mm to about 8 mm.

30. The urea production system according to paragraph 26 or 27, wherein the second membrane comprises a ceramic membrane.

31. The urea production system according to paragraph 30, wherein the ceramic membrane has a pore size of about 0.1 nm to about 5 nm and a thickness of about 0.5 mm to about 8 mm.

32. The urea production system according to paragraph 26 or 27, wherein the first membrane and the second membrane are ceramic membranes having a pore size of about 0.1 nm to about 5 nm and a thickness of about 0.5 mm to about 8 mm.

33. The urea production system according to any one of paragraphs 28 to 31, wherein the ceramic membrane is configured to separate a urea reaction mixture comprising urea, water, ammonia, carbon dioxide, and ammonium carbamate into an aqueous filtrate and a urea concentrate comprising urea, ammonia, carbon dioxide, and ammonium carbamate.

34. A urea production system, comprising: a pressurized mixer coupled to and in fluid communication independently with each of an ammonia source, a carbon dioxide source, and an ammonium carbamate source; a reactor coupled to and in fluid communication with the pressurized mixer, and a urea purification system in fluid communication with and disposed downstream of the reactor, wherein the reactor comprises a membrane, is coupled to and downstream of the pressurized mixer, and is coupled to and upstream of the urea purification system.

35. The urea production system according to paragraph 34, wherein the urea purification system comprises two or more separators and two or more decomposers.

36. The urea production system according to paragraph 34 or 35, wherein the membrane is a ceramic membrane.

37. The urea production system according to paragraph 34 or 35, wherein the membrane is a ceramic membrane having a pore size of about 0.1 nm to about 5 nm and a thickness of about 0.5 mm to about 8 mm.

38. The urea production system according to any one of paragraphs 34 to 37, wherein the membrane is configured to separate a urea reaction mixture comprising urea, water, ammonia, carbon dioxide, and ammonium carbamate into an aqueous filtrate and a urea concentrate comprising urea, ammonia, carbon dioxide, and ammonium carbamate.

Certain embodiments and features have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. And if applicable, all patents, test procedures, and other documents cited in this application are fully incorporated by reference to the extent such disclosure is not inconsistent with this application and for all jurisdictions in which such incorporation is permitted.

While the foregoing is directed to certain illustrative embodiments, other and further embodiments of the invention can be devised without departing from the basic scope thereof and the scope thereof is determined by the claims that follow.

What is claimed is:
1. A method for producing urea, comprising:
   combining ammonia, carbon dioxide, and a carbamate solution in a pressurized mixer to produce a carbamate reaction mixture comprising ammonium carbamate, ammonia, and carbon dioxide;
   transferring the carbamate reaction mixture from the pressurized mixer to a reactor;
   heating the carbamate reaction mixture in the reactor to produce a urea reaction mixture comprising urea, water, ammonia, carbon dioxide, and ammonium carbamate;

contacting the urea reaction mixture to a membrane to separate the urea reaction mixture into an aqueous filtrate and a urea concentrate comprising urea, ammonia, carbon dioxide, and ammonium carbamate;

transferring the urea concentrate from the reactor to a urea purification system, wherein the urea purification system comprises one or more separators and one or more decomposers; and flowing the urea concentrate through the urea purification system to produce a urea product and the carbamate solution, wherein the carbamate solution comprises ammonium carbamate, ammonia, and carbon dioxide; wherein about 60 wt % to about 95 wt % of the carbon dioxide introduced to the pressurized mixer is condensed to a liquefied state in the pressurized mixer and about 5 wt % to about 40 wt % of the carbon dioxide introduced to the pressurized mixer is transferred in a gaseous state to the reactor.

2. The method of claim 1, wherein prior to transferring the urea concentrate from the reactor to the urea purification system, the method further comprises:

transferring the urea concentrate through a plurality of isolated zones disposed in the reactor, wherein each isolated zone comprises an additional membrane;

heating the urea concentrate in each of the isolated zones to produce additional urea and water; and contacting the urea concentrate comprising the additional urea and water to the additional membrane disposed in each of the isolated zones to separate the urea concentrate comprising the additional urea and water into the aqueous filtrate and the urea concentrate.

3. The method of claim 2, further comprising collecting the aqueous filtrate from each of the membranes and combining the aqueous filtrates to produce a combined aqueous filtrate.

4. The method of claim 1, wherein prior to transferring the urea concentrate from the reactor to the urea purification system, the method further comprises:

transferring the urea concentrate through a plurality of isolated zones disposed in the reactor, wherein each of the plurality of isolated zones comprises a portion of the membrane;

heating the urea concentrate in each of the isolated zones to produce additional urea and water; and contacting the urea concentrate comprising the additional urea and water to the portion of the membrane disposed in each of the isolated zones to separate the urea concentrate comprising the additional urea and water into the aqueous filtrate and the urea concentrate.

5. The method of claim 1, wherein the membrane comprises a ceramic membrane.

6. The method of claim 5, wherein the ceramic membrane has a pore size of about 0.1 nm to about 5 nm and a thickness of about 0.5 mm to about 8 mm.

7. The method of claim 1, wherein the urea product comprises about 97 wt % to about 99.9 wt % of urea.

8. The method of claim 1, wherein the urea purification system comprises two or more separators and two or more decomposers.

9. The method of claim 1, wherein the carbamate reaction mixture is transferred from the pressurized mixer to the reactor through a first line, and wherein the carbon dioxide in the gaseous state is transferred from the pressurized mixer to the reactor through a second line that is different than the first line.

10. A method for producing urea, comprising:

combining ammonia and carbon dioxide in a pressurized mixer to produce a carbamate reaction mixture comprising ammonium carbamate, ammonia, and carbon dioxide;

transferring the carbamate reaction mixture from the pressurized mixer to a reactor, wherein the reactor comprises a first isolated zone, a second isolated zone, and a third isolated zone, and wherein the carbamate reaction mixture is transferred from the pressurized mixer to the first isolated zone;

heating the carbamate reaction mixture in the first isolated zone to produce a first urea reaction mixture comprising urea, water, ammonia, carbon dioxide, and ammonium carbamate;

contacting the urea reaction mixture to a first membrane disposed in the first isolated zone to separate the urea reaction mixture into a first aqueous filtrate and a first urea concentrate comprising urea, ammonia, carbon dioxide, and ammonium carbamate;

transferring the first urea concentrate to the second isolated zone;

heating the first urea concentrate in the second isolated zone to produce a second urea reaction mixture comprising urea, water, ammonia, carbon dioxide, and ammonium carbamate;

contacting the second urea reaction mixture with a second membrane disposed in the second isolated zone to separate the second urea reaction mixture into a second aqueous filtrate and a second urea concentrate comprising urea, ammonia, carbon dioxide, and ammonium carbamate;

transferring the second urea concentrate to the third isolated zone;

heating the second urea concentrate in the third isolated zone to produce a third urea reaction mixture comprising urea, water, ammonia, carbon dioxide, and ammonium carbamate;

contacting the third urea reaction mixture with a third membrane disposed in the third isolated zone to separate the third urea reaction mixture into a third aqueous filtrate and a third urea concentrate comprising urea, ammonia, carbon dioxide, and ammonium carbamate;

transferring the third urea concentrate from the reactor to a urea purification system; and flowing the third urea concentrate through the urea purification system to produce a urea product, wherein the urea product comprises about 95 wt % to about 99.99 wt % of urea.

11. The method of claim 10, wherein the urea product comprises about 97 wt % to about 99.9 wt % of urea.

12. The method of claim 10, further comprising combining a carbamate solution with the ammonia and the carbon dioxide in the pressurized mixer to produce the carbamate reaction mixture, wherein the carbamate solution comprises ammonium carbamate, ammonia, and carbon dioxide.

13. The method of claim 12, wherein flowing the third urea concentrate through the urea purification system further produces the carbamate solution.

14. The method of claim 12, wherein the carbamate reaction mixture in the first isolated zone is heated to a temperature of about 175° C. to about 210° C. and pressurized to a pressure of about 150 kg/cm$^2$ abs to about 210 kg/cm$^2$ abs to produce the first urea reaction mixture.

15. The method of claim 10, wherein the first membrane, the second membrane, or the third membrane is a ceramic membrane having a pore size of about 0.1 nm to about 5 nm and a thickness of about 0.5 mm to about 8 mm.

16. The method of claim 10, further comprising combining the first aqueous filtrate, the second aqueous filtrate, and the third aqueous filtrate to produce a combined aqueous filtrate.

17. The method of claim 16, wherein the combined aqueous filtrate comprises about 85 wt % to about 99 wt % of water, about 1 wt % to about 10 wt % of ammonia, about 0.1 wt % to about 8 wt % of carbon dioxide, and about 0.1 wt % to about 1.5 wt % of urea.

* * * * *